US010842174B2

(12) United States Patent
Durhuus et al.

(10) Patent No.: US 10,842,174 B2
(45) Date of Patent: Nov. 24, 2020

(54) METHOD FOR PRODUCING BIOMASS WHICH HAS A HIGH EXOPOLYSACCHARIDE CONTENT

(71) Applicant: Evonik Degussa GmbH, Essen (DE)

(72) Inventors: Thomas Durhuus, Copenhagen (DK); Stefan Eils, Gründau (DE); Amelia Claudia Silva, Hanau (DE); Horst Priefert, Ostbevern (DE); Jens Schneider, Bielefeld (DE); Christian Rabe, Grossostheim (DE)

(73) Assignee: Evonik Operations GmbH, Essen (DE)

( * ) Notice: Subject to any disclaimer, the term of this patent is extended or adjusted under 35 U.S.C. 154(b) by 185 days.

(21) Appl. No.: 15/516,058

(22) PCT Filed: Oct. 2, 2015

(86) PCT No.: PCT/EP2015/072824
§ 371 (c)(1),
(2) Date: Mar. 31, 2017

(87) PCT Pub. No.: WO2016/050965
PCT Pub. Date: Apr. 7, 2016

(65) Prior Publication Data
US 2017/0303561 A1 Oct. 26, 2017

(30) Foreign Application Priority Data
Oct. 2, 2014 (EP) .................................... 14187471

(51) Int. Cl.
A23K 20/163 (2016.01)
A23K 50/80 (2016.01)
A61K 35/66 (2015.01)
C12P 7/64 (2006.01)
A61K 31/202 (2006.01)
C12N 1/10 (2006.01)
C12P 19/04 (2006.01)
A23K 10/12 (2016.01)
A23K 40/25 (2016.01)
A23K 20/158 (2016.01)

(52) U.S. Cl.
CPC ............ *A23K 20/163* (2016.05); *A23K 10/12* (2016.05); *A23K 20/158* (2016.05); *A23K 40/25* (2016.05); *A23K 50/80* (2016.05); *A61K 31/202* (2013.01); *A61K 35/66* (2013.01); *C12N 1/10* (2013.01); *C12P 7/6472* (2013.01); *C12P 19/04* (2013.01); *Y02A 40/818* (2018.01)

(58) Field of Classification Search
CPC ...... A23K 20/163; A23K 50/80; A23K 10/12; A23K 40/25; A23K 20/158; C12N 1/10; C12P 19/04; C12P 7/6472; C12P 7/64; A61K 35/66; A61K 31/202; Y02A 40/818
See application file for complete search history.

(56) References Cited

U.S. PATENT DOCUMENTS

| | | |
|---|---|---|
| 2,123,134 A | 7/1938 | Cowgill |
| 2,177,031 A | 10/1939 | Tanner |
| 2,513,369 A | 7/1950 | Shaw |
| 3,257,737 A | 6/1966 | Thomas |
| 3,257,738 A | 6/1966 | Margittai et al. |
| 3,437,489 A | 4/1969 | Seiji et al. |
| 3,773,527 A | 11/1973 | Ruggerone |
| 3,920,815 A | 11/1975 | Harvey et al. |
| 4,160,040 A | 7/1979 | Luca et al. |
| 4,209,538 A | 6/1980 | Woodruff |
| 4,228,197 A | 10/1980 | Means |
| 4,335,150 A | 6/1982 | Hosaka et al. |
| 4,592,762 A | 6/1986 | Babu et al. |
| 4,683,139 A | 7/1987 | Cheng |
| 5,113,597 A | 5/1992 | Sylla |
| 5,130,242 A | 7/1992 | Barclay |
| 5,298,271 A | 3/1994 | Takashina et al. |
| 5,340,594 A | 8/1994 | Barclay |
| 5,340,742 A | 8/1994 | Barclay |
| 5,434,183 A | 7/1995 | Larsson-Backstrom |
| 5,518,918 A | 5/1996 | Barclay |
| 5,567,732 A | 10/1996 | Kyle et al. |
| 5,574,065 A | 11/1996 | Trimbo |
| 5,622,710 A | 4/1997 | Binder et al. |
| 5,656,319 A | 8/1997 | Barclay |
| 5,698,244 A | 12/1997 | Barclay |
| 5,700,506 A | 12/1997 | Mudahar |
| 5,700,837 A | 12/1997 | Trimbo |
| 5,840,358 A | 11/1998 | Hofler et al. |
| 6,068,874 A | 5/2000 | Grocholski |
| 6,117,905 A | 9/2000 | Higashiyama et al. |
| 6,158,147 A | 12/2000 | Smith et al. |
| 6,166,230 A | 12/2000 | Bijl et al. |
| 6,248,909 B1 | 6/2001 | Akimoto et al. |
| 6,255,505 B1 | 7/2001 | Bijl et al. |
| 6,326,037 B1 | 12/2001 | Mann et al. |
| 6,372,460 B1 | 4/2002 | Gladue et al. |
| 6,410,281 B1 | 6/2002 | Barclay |
| 6,441,208 B2 | 8/2002 | Bijl et al. |
| 6,451,567 B1 | 9/2002 | Barclay |
| 6,602,690 B2 | 8/2003 | Kawashima et al. |
| 6,607,900 B2 | 8/2003 | Bailey et al. |
| 6,727,373 B2 | 4/2004 | Bijl et al. |
| 6,812,009 B2 | 11/2004 | Gladue et al. |

(Continued)

FOREIGN PATENT DOCUMENTS

| | | |
|---|---|---|
| AU | 771 809 B2 | 6/2001 |
| CH | 646 729 | 12/1984 |

(Continued)

OTHER PUBLICATIONS

Jain et al., Mar Biotechnol, 2005, vol. 7, No. 3, p. 184-192.*

(Continued)

*Primary Examiner* — Kade Ariani
(74) *Attorney, Agent, or Firm* — Law Office of: Michael A. Sanzo, LLC

(57) ABSTRACT

According to the invention, it was found that culturing of cells of the taxon Labyrinthulomycetes in a high content of sulphate makes it possible to obtain a biomass having a high EPS content, which biomass can in addition be advantageously further processed into a feedstuff.

20 Claims, No Drawings

(56) References Cited

U.S. PATENT DOCUMENTS

| | | | |
|---|---|---|---|
| 6,977,167 B2 | 12/2005 | Barclay | |
| 7,067,145 B2 | 6/2006 | Place et al. | |
| 7,259,006 B2 | 8/2007 | Komazawa et al. | |
| 7,381,558 B2 | 6/2008 | Barclay | |
| 7,470,527 B2 | 12/2008 | Streekstra et al. | |
| 7,514,096 B2 | 4/2009 | Haraldsson et al. | |
| 7,514,244 B2 | 4/2009 | Tanaka et al. | |
| 7,579,174 B2 | 8/2009 | Bailey et al. | |
| 7,709,236 B2 | 5/2010 | Akimoto et al. | |
| 7,723,386 B2 | 5/2010 | Akimoto et al. | |
| 7,732,170 B2 | 6/2010 | Bailey et al. | |
| 7,847,113 B2 | 12/2010 | Kawashima et al. | |
| 7,863,026 B2 | 1/2011 | Komazawa et al. | |
| 7,910,604 B2 * | 3/2011 | Vazquez-Anon | A23K 50/10 424/438 |
| 7,935,365 B2 | 5/2011 | Dror et al. | |
| 8,030,348 B2 | 10/2011 | Sampalis | |
| 8,052,992 B2 | 11/2011 | Dror et al. | |
| 8,124,384 B2 | 2/2012 | Bailey et al. | |
| 8,124,385 B2 | 2/2012 | Bailey et al. | |
| 8,129,172 B2 | 3/2012 | Barclay | |
| 8,143,310 B2 | 3/2012 | Wang | |
| 8,163,515 B2 | 4/2012 | Burja et al. | |
| 8,187,846 B2 | 5/2012 | Bailey et al. | |
| 8,207,363 B2 | 6/2012 | Apt et al. | |
| 8,216,812 B2 | 7/2012 | Bailey et al. | |
| 8,217,151 B2 | 7/2012 | Schaap et al. | |
| 8,232,090 B2 | 7/2012 | Kallenmareth | |
| 8,236,854 B2 | 8/2012 | Akimoto et al. | |
| 8,241,868 B2 | 8/2012 | Higashiyama et al. | |
| 8,278,351 B2 | 10/2012 | Sampalis | |
| 8,288,133 B2 | 10/2012 | Bailey et al. | |
| 8,288,134 B2 | 10/2012 | Bailey et al. | |
| 8,334,363 B2 | 12/2012 | Hurd et al. | |
| 8,343,753 B2 | 1/2013 | Chilton et al. | |
| 8,367,774 B2 | 2/2013 | Frank | |
| 8,420,349 B2 | 4/2013 | Kralovec et al. | |
| 8,900,831 B2 | 12/2014 | Rusing et al. | |
| 8,945,886 B2 | 2/2015 | Katano et al. | |
| 8,999,663 B2 | 4/2015 | Avgousti et al. | |
| 9,045,785 B2 | 6/2015 | Pfeifer et al. | |
| 9,072,311 B2 | 7/2015 | Harel et al. | |
| 9,101,151 B2 | 8/2015 | Kobzeff et al. | |
| 9,414,612 B2 | 8/2016 | Apt et al. | |
| 9,493,798 B2 | 11/2016 | Higashiyama et al. | |
| 9,649,609 B2 | 5/2017 | Alt et al. | |
| 9,848,623 B2 | 12/2017 | Bailey et al. | |
| 10,531,679 B2 | 1/2020 | Rudinger | |
| 10,619,175 B2 | 4/2020 | Rabe | |
| 2002/0110582 A1 | 8/2002 | Place et al. | |
| 2003/0143659 A1 | 7/2003 | Bijl et al. | |
| 2003/0170371 A1 | 9/2003 | Jobe | |
| 2005/0118208 A1 | 6/2005 | Bewert | |
| 2005/0129739 A1 | 6/2005 | Kohn et al. | |
| 2005/0202148 A1 | 9/2005 | Streekstra et al. | |
| 2005/0287263 A1 | 12/2005 | Mayer | |
| 2006/0051484 A1 | 3/2006 | Yamaguchi et al. | |
| 2006/0068019 A1 | 3/2006 | Daiziel | |
| 2006/0094089 A1 | 5/2006 | Barclay | |
| 2006/0127531 A1 | 6/2006 | Jobe | |
| 2006/0160203 A1 | 7/2006 | Barclay | |
| 2006/0188969 A1 | 8/2006 | Barclay | |
| 2006/0265766 A1 | 11/2006 | Kyle et al. | |
| 2006/0286205 A1 | 12/2006 | Fichtali et al. | |
| 2007/0032383 A1 | 2/2007 | Newell | |
| 2007/0082008 A1 | 4/2007 | Harel et al. | |
| 2007/0092955 A1 | 4/2007 | De Laat et al. | |
| 2007/0172540 A1 | 7/2007 | Neece | |
| 2007/0243307 A1 | 10/2007 | Abril et al. | |
| 2007/0244192 A1 | 10/2007 | Metz | |
| 2007/0248738 A1 | 10/2007 | Abril et al. | |
| 2007/0248739 A1 | 10/2007 | Abril et al. | |
| 2008/0026128 A1 | 1/2008 | Yamaguchi et al. | |
| 2008/0032381 A1 | 2/2008 | Bailey et al. | |
| 2008/0038800 A1 | 2/2008 | Ruecker et al. | |
| 2008/0096964 A1 | 4/2008 | Subramanian et al. | |
| 2008/0166780 A1 | 7/2008 | Barclay | |
| 2008/0199923 A1 | 8/2008 | Barclay | |
| 2008/0254177 A1 | 10/2008 | Lin et al. | |
| 2009/0004219 A1 | 1/2009 | Kallenmareth | |
| 2009/0053342 A1 | 2/2009 | Streekstra et al. | |
| 2009/0064567 A1 | 3/2009 | Lippmeier et al. | |
| 2009/0136637 A1 | 5/2009 | Janssen et al. | |
| 2009/0162892 A1 | 6/2009 | Pompejus et al. | |
| 2009/0182050 A1 | 7/2009 | Barrow et al. | |
| 2009/0202672 A1 | 8/2009 | Hartnell | |
| 2009/0263889 A1 | 10/2009 | Wumpelmann | |
| 2009/0274817 A1 | 11/2009 | Yamaguchi et al. | |
| 2009/0285969 A1 | 11/2009 | Schaap et al. | |
| 2010/0010088 A1 | 1/2010 | Chilton et al. | |
| 2010/0086638 A1 | 4/2010 | Kyle et al. | |
| 2010/0151112 A1 | 6/2010 | Franklin et al. | |
| 2010/0159583 A1 | 6/2010 | Onose | |
| 2010/0239712 A1 | 9/2010 | Brooks et al. | |
| 2010/0266681 A1 | 10/2010 | Holmeide | |
| 2010/0285105 A1 | 11/2010 | Radianingtyas | |
| 2010/0297292 A1 | 11/2010 | Brooks et al. | |
| 2010/0297295 A1 | 11/2010 | Brooks et al. | |
| 2010/0297323 A1 | 11/2010 | Brooks et al. | |
| 2010/0297331 A1 | 11/2010 | Brooks et al. | |
| 2010/0303961 A1 | 12/2010 | Brooks et al. | |
| 2010/0303989 A1 | 12/2010 | Brooks et al. | |
| 2010/0303990 A1 | 12/2010 | Brooks et al. | |
| 2011/0054029 A1 | 3/2011 | Kuhrts | |
| 2011/0086128 A1 | 4/2011 | Abril et al. | |
| 2011/0117068 A1 | 5/2011 | Lang et al. | |
| 2011/0129884 A1 | 6/2011 | Luy | |
| 2011/0166228 A1 | 7/2011 | Holmeide et al. | |
| 2011/0177031 A1 | 7/2011 | Apt et al. | |
| 2011/0189228 A1 | 8/2011 | Bayne et al. | |
| 2011/0195448 A1 | 8/2011 | Lippmeier et al. | |
| 2011/0195449 A1 | 8/2011 | Lippmeier et al. | |
| 2011/0203168 A1 | 8/2011 | Franklin et al. | |
| 2011/0258915 A1 | 10/2011 | Subhadra | |
| 2011/0287158 A1 | 11/2011 | Yamaguchi et al. | |
| 2012/0213905 A1 | 8/2012 | Nichols | |
| 2012/0237578 A1 | 9/2012 | Lei et al. | |
| 2013/0045226 A1 | 2/2013 | Avgousti et al. | |
| 2013/0046020 A1 | 2/2013 | Liang et al. | |
| 2013/0046105 A1 | 2/2013 | Avgousti et al. | |
| 2013/0172590 A1 | 7/2013 | Pfeifer et al. | |
| 2013/0302470 A1 | 11/2013 | Becker et al. | |
| 2014/0017742 A1 | 1/2014 | Streekstra et al. | |
| 2015/0044356 A1 | 2/2015 | Bootsma et al. | |
| 2015/0223492 A1 | 8/2015 | Pfeifer et al. | |
| 2016/0066600 A1 | 3/2016 | Barrows | |
| 2016/0183565 A1 | 6/2016 | Rudinger et al. | |
| 2016/0227816 A1 | 8/2016 | Alt et al. | |
| 2016/0249642 A1 | 9/2016 | Rabe et al. | |
| 2016/0255862 A1 | 9/2016 | Oelmann et al. | |
| 2017/0121742 A1 | 5/2017 | Aijawi et al. | |
| 2017/0245523 A1 | 8/2017 | Pfeifer et al. | |
| 2017/0290356 A1 | 10/2017 | Silva et al. | |
| 2017/0295823 A1 | 10/2017 | Rabe et al. | |
| 2017/0295824 A1 | 10/2017 | Priefert et al. | |
| 2017/0298318 A1 | 10/2017 | Rabe et al. | |
| 2017/0306365 A1 | 10/2017 | Rabe et al. | |
| 2019/0300818 A1 | 10/2019 | Bärz | |
| 2019/0323043 A1 | 10/2019 | Diehl | |

FOREIGN PATENT DOCUMENTS

| | | |
|---|---|---|
| CN | 101 999 552 | 4/2011 |
| CN | 102 687 810 | 9/2012 |
| CN | 102919512 | 2/2013 |
| CN | 103 070 293 | 5/2013 |
| CN | 103 385 390 | 11/2013 |
| DE | 10 2006 026 328 | 1/2008 |
| GB | 1 397 410 | 6/1975 |
| GB | 1 560 478 | 10/1976 |
| GB | 2 324 701 | 11/1998 |
| GB | 2 437 909 | 11/2007 |
| WO | WO 91/07498 | 5/1991 |
| WO | WO 94/08467 | 4/1994 |

(56) References Cited

FOREIGN PATENT DOCUMENTS

| | | |
|---|---|---|
| WO | WO 97/36996 | 10/1997 |
| WO | WO 97/37032 | 10/1997 |
| WO | WO 98/49904 | 11/1998 |
| WO | WO 01/54510 | 8/2001 |
| WO | WO 02/00035 | 1/2002 |
| WO | WO 2006/085672 | 8/2006 |
| WO | WO 2006/124598 | 11/2006 |
| WO | WO 2006/136539 | 12/2006 |
| WO | WO 2007/074479 | 7/2007 |
| WO | WO 2007/117511 | 10/2007 |
| WO | WO 2008/019887 | 2/2008 |
| WO | WO 2008/049512 | 5/2008 |
| WO | WO 2008/148873 | 12/2008 |
| WO | WO 2010/090979 | 8/2010 |
| WO | WO 2010/120923 | 10/2010 |
| WO | WO 2010/128312 | 11/2010 |
| WO | WO 2011/006261 | 1/2011 |
| WO | WO 2013/022485 | 2/2013 |
| WO | WO 2014/045191 | 3/2014 |
| WO | WO 2014/122087 | 8/2014 |
| WO | WO 2014/122092 | 8/2014 |

OTHER PUBLICATIONS

Chang, K.J. L. , Thesis Aug. 2013, 199 pages of PDF.*
Restriction requirement for copending U.S. Appl. No. 15/516,044, dated Oct. 25, 2018.
Suomalainen, et al., "The Fatty Acid Composition of Baker's and Brewer's Yeast," *Chem. Phys. Lipids 2*:296-315 (1968).
Technicial Information 1251 (2017) http://www.sipernat.com/sites/lists/RE/DocumentsSI/TI-1251-AEROSIL-and-SIPERNAT-Silica-Versatile-Raw-Materials-for-Personal-Care-Formulations-EN.pdf download Apr. 11, 2018 (Year: 2017).
English language translation International Search Report for PCT/EP2015/072824 filed Oct. 2, 2015.
English language translation of the Written Opinion of the International Searching Authority for PCT/EP2015/072824 filed Oct. 2, 2015.
English language translation of the International Preliminary Report on Patentability for PCT/EP2015/072824 filed Oct. 2, 2015.
European Search Report for EP 14 18 7471 filed Oct. 2, 2014.
English translation of the International Search Report for PCT/EP2015/071666 filed Sep. 22, 2015 for copending U.S. Appl. No. 15/516,022.
English language translation of the Written Opinion of the International Searching Authority for PCT/EP2015/071666 filed Sep. 22, 2015 for copending U.S. Appl. No. 15/516,022.
English language translation of the International Preliminary Report on Patentability for PCT/EP2015/071666 filed Sep. 22, 2015 for copending U.S. Appl. No. 15/516,022.
European Search Report with partial machine translation for EP 14 18 7485 filed Oct. 2, 2014 for copending U.S. Appl. No. 15/516,022.
English translation of the International Search Report for PCT/EP2015/071707 filed Sep. 22, 2015 for copending U.S. Appl. No. 15/516,044.
English language translation of the Written Opinion of the International Searching Authority for PCT/EP2015/071707 filed Sep. 22, 2015 for copending U.S. Appl. No. 15/516,044.
English language translation of the International Preliminary Report on Patentability for PCT/EP2015/071707 filed Sep. 22, 2015 for copending U.S. Appl. No. 15/516,044.
European Search Report with partial machine translation for EP 14 18 7479 filed Oct. 2, 2014 for copending U.S. Appl. No. 15/516,044.
English translation of the International Search Report for PCT/EP2015/071689 filed Sep. 22, 2015 for copending U.S. Appl. No. 15/516,023.
English language translation of the Written Opinion of the International Searching Authority for PCT/EP2015/071689 filed Sep. 22, 2015 for copending U.S. Appl. No. 15/516,023.
English language translation of the International Preliminary Report on Patentability for PCT/EP2015/071689 filed Sep. 22, 2015 for copending U.S. Appl. No. 15/516,023.
European Search Report with partial machine translation for EP 14 18 7467 filed Oct. 2, 2014 for copending U.S. Appl. No. 15/516,023.
English translation of the International Search Report for PCT/EP2015/071635 filed Sep. 22, 2015 for copending U.S. Appl. No. 15/516,024.
English language translation of the Written Opinion of the International Searching Authority for PCT/EP2015/071635 filed Sep. 22, 2015 for copending U.S. Appl. No. 15/516,024.
English language translation of the International Preliminary Report on Patentability for PCT/EP2015/071635 filed Sep. 22, 2015 for copending U.S. Appl. No. 15/516,024.
European Search Report with partial machine translation for EP 14 18 7471 filed Oct. 2, 2014 for copending U.S. Appl. No. 15/516,024.
Asha, et al., "Effect of sea weed, sea grass and powdered algae in rearing the hatchery produced juveniles of *Holothuria* (metriatyla) *scabra*, jeager," *Proceedings of the National Symposium on Recent Trends in Fisheries*, (2004).
Baeverfjord, et al., "Low feed pellet water stability and fluctuating water salinity cause separation and accumulation of dietary oil in the stomach of rainbow trout (*Oncorhrynchus* mykiss)," *Aquaculture* 261(4) :1335-1345 (Dec. 2006).
Carper, et al., "Potential of Thraustochytrids to Partially Replace Fish Oil in Atlantic Salmon Feeds," *Marine Biotechnology* 5:480-492 (Oct. 2002).
Hondo, et al., "*Schizochyfrium limacinum* sp. nov., a new thraustochytrid from a mangrove area in the west Pacific Ocean," *Mycological Research* 102(4):439-448 (Apr. 1998).
Jain, et al., "Extracellular Polysaccharide Production by Thraustochytrid Protists," *Marine Biotechnology* 7:184-192 (published online May 2005).
Miller, et al., Replacement of fish oil with thraustochytrid *Schizochytrium* sp. L oil in Atlantic salmon parr (*Salmo* salar L) diets, *Comparative Biochemistry and Physiology, Part A* 148:382-392 (available online May 2007).
Nakahara, et al., "Production of Docosahexaenoic and Docosapentaenioc Acids by *Schizochyfrium* sp. Isolated from Yap Islands," *Journal of American Oil Chemists' Society* 73(11):1421-1425 (Nov. 1996).
Prabu, et al., "Effect of sodium sulphate salinity for production of docosahexaenoic acid (DHA) by *Thraustochytrids aureum* RAK-21," *Asian Biomedicine* 6(5):693-701 (Oct. 2012).
Taxonomy Browser: *Aurantiochytrium limacinum*; taxonomy ID: 87102 (Jan. 2015).
XP-002721747; Database WPI Thomson Scientific, London GB; (Sep. 2013).
XP-002534705; Degussa: "Product Information Sipernat D17," Internet citation (Sep. 2004).
U.S. Appl. No. 14/904,665, filed Jan. 12, 2016, US-2016/0183565, Jun. 30, 2016, Rudinger.
U.S. Appl. No. 15/027,429, filed Apr. 5, 2016, US-2016/0249642, Sep. 1, 2016, Rabe.
U.S. Appl. No. 15/516,038, filed Mar. 31, 2017, Rabe.
U.S. Appl. No. 15/516,024, filed Mar. 31, 2017, Priefert.
U.S. Appl. No. 15/516,044, filed Mar. 31, 2017, Rabe.
U.S. Appl. No. 15/516,022, filed Mar. 31, 2017, Rabe.
U.S. Appl. No. 15/516,023, filed Mar. 31, 2017, Silva.
Hammond, et al., "Safety Assessment of DHA-Rich Microalgae from *Schizochytrium* sp.," *Regulatory Toxicology and Pharmacology* 33(2):192-204 (Apr. 2001).
Chen, et al., "Whole cell algae powder used for increasing docosahexanoic acid content in milk of high-yielding mammal, comprises docohexanoic acid containing algae cell slurry, emulsifier, antioxidant, filler, packaging material, dispersant and water," WPI/THOMPSON, Bd. 2011, Nr. 44, (Apr. 6, 2011); XP-002721747.
Uemura, "Synthesis and production of unsaturated and polyunsaturated fatty acids in yeast: current state and perspectives," *Appl. Microbiol. Biotechnol.* 95:1-12 (May 2012).
Visentainer, et al., "Influence of diets enriched with flaxseed oil on the α-linolenic, eicosapentaenoic and docosahexaenoic fatty acid in Nile tilapia (*Oreochromis niloticus*)," *Food Chemistry* 90:557-560 (May 2005).

(56) References Cited

OTHER PUBLICATIONS

Response to Restriction requirement for copending U.S. Appl. No. 15/516,044, filed Dec. 25, 2018.
Amendment to accompany Response to Restriction requirement for copending U.S. Appl. No. 15/516,044, filed Dec. 25, 2018.
Restriction Requirement for copending U.S. Appl. No. 15/516,024, dated Mar. 4, 2019.
Non Final Office Action for copending U.S. Appl. No. 15/516,044, dated Mar. 27, 2019.
Response to Restriction Requirement for copending U.S. Appl. No. 15/516,024, filed May 4, 2019.
Restriction Requirement for copending U.S. Appl. No. 15/516,023, dated May 7, 2019.
Restriction Requirement for copending U.S. Appl. No. 15/516,022, dated Jun. 26, 2019.
Response to Restriction Requirement filed Jul. 5, 2019, for copending U.S. Appl. No. 15/516,023.
Response to Office Action filed Aug. 10, 2019 for copending U.S. Appl. No. 15/516,044.
Keleb, et al., "Continous twin screw extrusion for the wet granulation of lactose," *International Journal of Pharmaceutics* 239:69-80 (2002).
Office Action for copending U.S. Appl. No. 15/516,023, dated Aug. 6, 2019.
Non Final Office Action dated Aug. 16, 2019 for copending U.S. Appl. No. 15/516,024.
Response to Non Final Office Action filed Dec. 16, 2019 for copending U.S. Appl. No. 15/516,024.
Final Rejection dated Mar. 19, 2020 for copending U.S. Appl. No. 15/516,024.
Response to Restriction Requirement filed Aug. 26, 2019 for copending U.S. Appl. No. 15/516,022.
Non Final Office Action dated Sep. 17, 2019 for copending U.S. Appl. No. 15/516,022.
Response to Non Final Office Action filed Jan. 9, 2020 for copending U.S. Appl. No. 15/516,022.
Final Rejection dated Feb. 13, 2020 for copending U.S. Appl. No. 15/516,022.
Response to Non Final Office Action filed Nov. 24, 2019 for copending U.S. Appl. No. 15/516,023.
Final Rejection dated Mar. 4, 2020 for copending U.S. Appl. No. 15/516,023.
U.S. Appl. No. 16/317,305, filed Jan. 11, 2019, Bärz.
U.S. Appl. No. 16/639,529, filed Feb. 14, 2020, Burja.
U.S. Appl. No. 16/644,443, filed Mar. 4, 2020, Bahl.
Amendment & Response to Final Office Action filed Jul. 13, 2020 for copending U.S. Appl. No. 15/516,022.
Request for Continued Examination filed Jul. 13, 2020 for copending U.S. Appl. No. 15/516,022.

\* cited by examiner

METHOD FOR PRODUCING BIOMASS WHICH HAS A HIGH EXOPOLYSACCHARIDE CONTENT

CROSS REFERENCE TO RELATED APPLICATIONS

The present application is US national stage of international application, which PCT/EP2015/072824 had an international filing date of Oct. 2, 2015, and which was published in German under PCT Article 21(2) on Apr. 7, 2016. Priority is claimed to European application EP 14187471.9, filed on Oct. 2, 2014.

The present invention relates to a process for producing a biomass containing cells of the taxon Labyrinthulomycetes and having a high EPS content.

Processes for producing biomass containing cells of the taxon Labyrinthulomycetes have already been described in the prior art.

Jain et al. state that said cells are capable of producing so-called exopolysaccharides (EPSs) and of secreting them into the surrounding medium (Jain et al., Marine Biotechnology 7, 184-192 (2005)).

WO 2007/074479 describes a Schizochytrium limacinum strain which exhibits an increased production of EPS.

Exopolysaccharides (EPSs; also referred to as "extracellular polysaccharides" or "extracellular polymeric substances") represent a substance which has various possible medical uses attributed thereto, such as, for example, an antitumour action, or action as an anticoagulant or as a wound-healing promoter. In addition to use in the medical sphere, possible non-medical uses are also known, such as, for example, use as an emulsion stabilizer or foam stabilizer. Furthermore, it is assumed that EPSs also have a health-promoting action when used as feed additive in animal feeding.

It is an object of the present invention to provide a process for the increased production of EPS using cells of the taxon Labyrinthulomycetes or to provide a Labyrinthulomycetes-containing biomass having an increased content of EPS.

According to the invention, it was found that, surprisingly, the amount of EPS produced can be specifically increased by adding sulphate to the fermentation medium, even when high biomass densities are attained in the final fermentation broth.

In this connection, it became apparent that an optimal EPS yield can be attained by adding sulphate in an amount such that a sulphate concentration of 25 to 60 g/kg ensues in the resulting biomass.

A particular advantage of the thus obtained EPS-containing biomass is that the thus obtained biomass contains not only the EPS, but also polyunsaturated fatty acids (PUFAs) as a further valuable health-promoting ingredient.

Furthermore, the high EPS content brings about a high cell stability, preventing a premature release of the PUFAs into the fermentation broth.

Also, it became apparent that the biomass obtained which has a sulphate concentration of 25 to 60 g/kg can be further processed at a very low energy input into a feedstuff with high abrasion resistance and high water stability.

Another object of the present invention can therefore be considered that of providing a biomass which, owing to its properties, is suited to an especially good extent to being able to be further processed into a feedstuff.

The present invention therefore firstly provides a process for producing an exopolysaccharide (EPS) and preferably polyunsaturated fatty acid (PUFA)-containing biomass, characterized in that production of the biomass comprises culturing microorganisms of the taxon Labyrinthulomycetes in a fermentation medium containing sulphate in an amount such that a sulphate concentration, based on the dry mass, of 25 to 60 g/kg ensues in the resulting biomass. In this connection, the sulphate concentration in the resulting biomass is preferably 25 to 50 g/kg, in particular 25 to 40 g/kg, especially preferably 25 to 35 g/kg, based in each case on the dry mass.

According to the invention, it is particularly advantageous that a distinct increase in EPS production can be realized even at a very high biomass density. Therefore, in one embodiment preferred according to the invention, a biomass density of more than 50, 60 or 70 g, particularly preferably more than 80 or 90 g, above all more than 100 g, per litre of resulting fermentation broth is realized.

Owing to the simultaneously realizable high biomass yield, there is a further increase in the absolute EPS yield.

The present invention similarly further provides an EPS and preferably PUFA-containing biomass which contains cells of the taxon Labyrinthulomycetes and is obtainable using a process according to the invention.

The present invention similarly provides an EPS and preferably PUFA-containing biomass which contains cells of the taxon Labyrinthulomycetes and has a sulphate content of 25 to 60 g/kg, based on the dry mass, and is obtainable preferably by a process described above. The sulphate content is preferably 25 to 50 g/kg, in particular 25 to 40 g/kg, especially preferably 25 to 35 g/kg, based in each case on the dry mass.

According to the invention, "sulphate content" is to be understood to mean the total content of sulphate, i.e. the content of free and bound, in particular organically bound, sulphate. It can be assumed that the majority of the sulphate present in the biomass is present as a constituent of exopolysaccharides, which are involved in the formation of the cell wall of microorganisms. The amount of incorporated sulphate therefore represents a direct indication of the amount of synthesized EPS.

According to the invention, the sulphate content is preferably determined by ascertaining the sulphur content of the biomass obtained, since the majority of the sulphur present in the biomass can be attributed to the sulphate present. Sulphur which can be attributed to other sources can be disregarded owing to the amount of sulphate present. Thus, the amount of sulphate present and hence also the amount of EPS formed can be readily ascertained from the amount of sulphur ascertained.

In this connection, the sulphur content of the biomass is preferably determined by elemental analysis in accordance with DIN EN ISO 11885. For the analysis of the sulphur content of the biomass, appropriate aliquots of sample are disrupted preferably with nitric acid and hydrogen peroxide at 240° C. under pressure prior to the analysis in order to ensure the free accessibility of the sulphur present.

The present invention therefore also further provides a process for producing an EPS and preferably PUFA-containing biomass, characterized in that production of the biomass comprises culturing microorganisms in a fermentation medium containing sulphate in an amount such that a sulphur content of 8 to 20 g/kg, based on the dry mass, can be detected in the resulting biomass by elemental analysis in accordance with DIN EN ISO 11885. In this connection, the sulphur content in the resulting biomass is preferably 8 to 17 g/kg, in particular 8 to 14 g/kg, especially preferably 8 to 12 g/kg, based in each case on the dry mass.

The present invention therefore also further provides an EPS and preferably PUFA-containing biomass, characterized in that a sulphur content of 8 to 20 g/kg, based on the dry mass, can be detected by elemental analysis in accordance with DIN EN ISO 11885. In this connection, the sulphur content in the resulting biomass is preferably 8 to 17 g/kg, in particular 8 to 14 g/kg, especially preferably 8 to 12 g/kg, based in each case on the dry mass.

According to the invention, the phosphorus content of biomasses according to the invention is, with regard to the dry mass, preferably 1 to 6 g/kg, in particular 2 to 5 g/kg. The phosphorus content is preferably likewise ascertained by elemental analysis in accordance with DIN EN ISO 11885.

A biomass according to the invention preferably comprises cells, and preferably consists substantially of those cells of the taxon Labyrinthulomycetes (Labyrinthulea, slime nets), in particular those of the family of the Thraustochytriaceae. The family of the Thraustochytriaceae includes the genera *Althomia, Aplanochytrium, Elnia, Japonochytrium, Schizochytrium, Thraustochytrium, Aurantiochytrium, Oblongichytrium* and *Ulkenia*. Particular preference is given to cells of the genera *Thraustochytrium, Schizochytrium, Aurantiochytrium* or *Oblongichytrium*, especially those of the genus *Aurantiochytrium*. A particularly preferred strain is the strain *Aurantiochytrium limacinum* SR21 (IFO 32693).

The biomass according to the invention preferably takes the form of the product of a fermentative culturing process. Accordingly, the biomass may contain not only the cells to be disrupted but also constituents of the fermentation medium. These constituents may take the form of, in particular, salts, antifoam agents and unreacted carbon source and/or nitrogen source. The cell content in this biomass is preferably at least 70% by weight, preferably at least 75% by weight. Optionally, the cell content in the biomass may be increased by suitable wash steps to, for example, at least 80 or at least 90% by weight.

The cells in the biomass are preferably distinguished by the fact that they contain at least 20% by weight, preferably at least 30% by weight, in particular at least 35% by weight, of PUFAs, based in each case on the cell dry mass.

In a preferred embodiment, the majority of the lipids is present in the form of triglycerides, with preferably at least 50% by weight, in particular at least 75% by weight and, in an especially preferred embodiment, at least 90% by weight of the lipids present in the cell being present in the form of triglycerides.

Preferably, at least 10% by weight, in particular at least 20% by weight, especially preferably 20 to 60% by weight, in particular 20 to 40% by weight, of the fatty acids present in the cell are PUFAs.

According to the invention, polyunsaturated fatty acids (PUFAs) are understood to mean fatty acids having at least two C—C double bonds. According to the invention, highly unsaturated fatty acids (HUFAs) are preferred among the PUFAs. According to the invention, HUFAs are understood to mean fatty acids having at least four C—C double bonds.

The PUFAs may be present in the cell in free form or in bound form. Examples of the presence in bound form are phospholipids and esters of the PUFAs, in particular monoacyl-, diacyl- and triacylglycerides. In a preferred embodiment, the majority of the PUFAs is present in the form of triglycerides, with preferably at least 50% by weight, in particular at least 75% by weight and, in an especially preferred embodiment, at least 90% by weight of the PUFAs present in the cell being present in the form of triglycerides.

Preferred PUFAs are omega-3 fatty acids and omega-6 fatty acids, with omega-3 fatty acids being especially preferred. Preferred omega-3 fatty acids here are the eicosapentaenoic acid (EPA, 20:5ω-3), particularly the (5Z,8Z,11Z,14Z,17Z)-eicosa-5,8,11,14,17-pentaenoic acid, and the docosahexaenoic acid (DHA, 22:6ω-3), particularly the (4Z,7Z,10Z,13Z,16Z,19Z)-docosa-4,7,10,13,16,19-hexaenoic acid, with the docosahexaenoic acid being especially preferred.

Processes for producing the PUFA-containing cells especially of the order Thraustochytriales have been described in detail in the prior art (see, for example, WO91/07498, WO94/08467, WO97/37032, WO97/36996, WO01/54510). As a rule, the production takes place by cells being cultured in a fermenter in the presence of a carbon source and of a nitrogen source. In this context, biomass densities of more than 100 grams per litre and production rates of more than 0.5 gram of lipid per litre per hour may be attained. The process is preferably carried out as what is known as a fed-batch process, i.e. the carbon and nitrogen sources are fed in incrementally during the fermentation. Once the desired biomass has been obtained, lipid production may be induced by various measures, for example by limiting the nitrogen source, the carbon source or the oxygen content or combinations of these.

Suitable carbon sources are both alcoholic and non-alcoholic carbon sources. Examples of alcoholic carbon sources are methanol, ethanol and isopropanol. Examples of non-alcoholic carbon sources are fructose, glucose, sucrose, molasses, starch and corn syrup.

Suitable nitrogen sources are both inorganic and organic nitrogen sources. Examples of inorganic nitrogen sources are nitrates and ammonium salts, in particular ammonium sulphate and ammonium hydroxide. Examples of organic nitrogen sources are amino acids, in particular glutamate, and urea.

According to the invention, the desired sulphate content in the resulting biomass may be achieved in different ways.

For example, in what is known as a batch process, the required amount of sulphate may be initially charged in full right at the start. The amount of sulphate required can be easily calculated, since the cells used to form the biomass virtually completely assimilate the sulphate.

When using what is known as a fed-batch process, the amount of sulphate required may alternatively be metered in during the course of fermentation or, accordingly, some of the sulphate may be initially charged and the remainder metered in during the course of fermentation.

Especially when it emerges during the course of fermentation that the amount of biomass produced exceeds the originally calculated value, it is possible to ensure by subsequent metering-in of sulphate that the resulting biomass has sufficient cell stability.

According to the invention, the sulphate salt used is preferably sodium sulphate, ammonium sulphate or magnesium sulphate and also mixtures thereof.

During fermentation, the chloride content is, with regard to the liquid fermentation medium including the biomass present, preferably always below 3 g/kg, in particular below 1 g/kg, especially preferably below 400 mg/kg of fermentation medium.

In addition to sulphates and any chlorides used, it is also optionally possible during fermentation to use further salts, especially those selected from sodium carbonate, sodium hydrogen carbonate, soda ash or inorganic phosphorus compounds.

If further salts are used, these are preferably used in an amount such that each one during fermentation, with regard to the liquid fermentation medium including the biomass present, is present in each case in an amount of always less than 10 g/kg, in particular less than 5 g/kg, especially preferably less than 3 g/kg in the fermentation medium.

According to the invention, the total salt content in the fermentation medium including the biomass present is preferably always below 35 g/kg, in particular below 30 g/kg, during the course of the entire fermentation process. Especially preferably, the total salt content during the entire fermentation process, with regard to the liquid fermentation medium including the biomass present, is between 10 and 35 g/kg, in particular between 12 and 30 g/kg.

According to the invention, the sulphate content in the fermentation medium including the biomass present is preferably always between 5 and 16 g/kg during the course of the entire fermentation process.

In addition, organic phosphorus compounds and/or known growth-stimulating substances, such as, for example, yeast extract or corn steep liquor, may also be added to the fermentation medium so as to have a positive effect on the fermentation.

The cells are preferably fermented at a pH of 3 to 11, in particular 4 to 10, and preferably at a temperature of at least 20° C., in particular 20 to 40° C., especially preferably at least 30° C. A typical fermentation process takes up to approximately 100 hours.

According to the invention, the cells are preferably fermented up to a biomass density of at least 50, 60 or 70 g/l, in particular at least 80 or 90 g/l, especially preferably at least 100 g/l. In this case, the data are based on the content of dry biomass in relation to the total volume of the fermentation broth after the fermentation has ended. The content of dry biomass is determined by filtering-off of the biomass from the fermentation broth, subsequent washing with water, then complete drying—for example in a microwave—and lastly ascertainment of the dry weight.

After harvesting the cells or optionally even shortly before harvesting the cells, the cells are preferably pasteurized in order to kill the cells and to inactivate enzymes which might promote lipid degradation.

After the fermentation has ended, the biomass is harvested. By means of centrifugation, filtration, decanting or solvent evaporation, it is possible to remove the majority of the fermentation medium from the biomass. Solvent evaporation is preferably achieved using a drum dryer, a tunnel dryer, by means of spray drying or vacuum evaporation. In particular, solvent evaporation may also be achieved using a rotary evaporator, a thin-film evaporator or a falling-film evaporator. A useful alternative to solvent evaporation is, for example, reverse osmosis for concentrating the fermentation broth. Subsequently, the biomass obtained is optionally further dried, preferably by means of fluidized bed granulation. Preferably, the moisture content is reduced to below 15% by weight, in particular to below 10% by weight, especially preferably to below 5% by weight, by the drying process.

According to the invention, "dry mass" is accordingly preferably to be understood to mean a biomass having a moisture content of below 10% by weight, in particular below 5% by weight.

In a particularly preferred embodiment of the invention, the biomass is dried in accordance with the invention in a fluidized bed granulation process or a nozzle spray drying process, as described in EP13176661.0 for example.

During the drying process, silica may optionally be added to the biomass as anti-caking agent so that the biomass can be converted to an easier-to-manage state. For this purpose, the fermentation broth comprising biomass and also the silica are preferably sprayed into the particular drying zone. Alternatively, the biomass is preferably mixed with the silica only after the drying process. In this regard, reference is also made in particular to the patent application EP13187631.0.

A free-flowing, fine-grained or coarse-grained product, preferably a granulate, is preferably obtained by the drying process. A product having the desired particle size can optionally be obtained from the granulate obtained by sieving or dust separation.

Providing a free-flowing fine-grained powder was obtained, this can optionally be converted into a coarse-grained, free-flowing and largely dust-free product, which can be stored, by suitable compacting or granulating processes.

Conventional organic or inorganic auxiliaries or supports such as starch, gelatin, cellulose derivatives or similar substances, which are typically used in food processing or feed processing as binding agents, gelling agents or thickeners, may optionally be used in this subsequent granulation or compacting process.

"Free-flowing" according to the invention is understood to mean a powder that can flow out unhindered from a series of glass efflux vessels having different size outflow openings, at least from the vessel having the 5 millimetre opening (Klein: Seifen, Öle, Fette, Wachse 94, 12 (1968)).

"Fine-grained" according to the invention is understood to mean a powder having a predominant fraction (>50%) of particle sizes of 20 to 100 micrometres in diameter.

"Coarse-grained" according to the invention is understood to mean a powder having a predominant fraction (>50%) of particle sizes of 100 to 2500 micrometres in diameter.

"Dust-free" according to the invention is understood to mean a powder that contains only low fractions (<10%, preferably <5%) of particle sizes below 100 micrometres.

Particle sizes are preferably determined according to the invention by laser diffraction spectrometric methods. Possible methods are described in the textbook "Teilchengrößenmessung in der Laborpraxis" [Particle size measurement in the laboratory] by R. H. Müller and R. Schuhmann, Wissenschaftliche Verlagsgesellschaft Stuttgart (1996) and in the textbook "Introduction to Particle Technology" by M. Rhodes, Wley & Sons (1998). Inasmuch as various methods can be used, the first-cited usable method from the textbook by R. H. Müller and R. Schuhmann for the measuring of particle size is preferably used.

The products obtained by the drying process according to the invention preferably have a fraction of at least 80% by weight, particularly at least 90% by weight, particularly preferably at least 95% by weight, of particles having a particle size of 100 to 3500 micrometres, preferably 100 to 3000 micrometres, above all 100 to 2500 micrometres.

The products of a fluidized bed granulation process obtained according to the invention preferably have in this case a fraction of at least 80% by weight, particularly at least 90% by weight, particularly preferably at least 95% by weight, of particles having a particle size of 200 to 3500 micrometres, preferably 300 to 3000 micrometres, above all 500 to 2500 micrometres.

The products of a spray drying process obtained according to the invention preferably have in contrast a fraction of at least 80% by weight, particularly at least 90% by weight, particularly preferably at least 95% by weight, of particles having a particle size of 100 to 500 micrometres, preferably 100 to 400 micrometres, above all 100 to 300 micrometres.

The products of a spray drying process and subsequent granulation process obtained according to the invention preferably have a fraction of at least 80% by weight, particularly at least 90% by weight, particularly preferably at least 95% by weight, of particles having a particle size of 100 to 1000 micrometres.

The fraction of dust, i.e. particles having a particle size of less than 100 micrometres, is preferably at most 10% by weight, particularly at most 8% by weight, particularly preferably at most 5% by weight, above all at most 3% by weight.

The bulk density of the products according to the invention is preferably from 400 to 800 kg/m$^3$, particularly preferably from 450 to 700 kg/m$^3$.

According to the invention, it became apparent in particular that a biomass according to the invention can be further processed at low energy input into a feedstuff with high oil load capacity, high abrasion resistance and high water stability.

The present invention therefore also further provides a feedstuff comprising a biomass according to the invention and also further feedstuff ingredients.

In this connection, the further feedstuff ingredients are preferably selected from protein-containing, carbohydrate-containing, nucleic-acid-containing and lipid-soluble components and, if appropriate, further fat-containing components and furthermore from among other additives such as minerals, vitamins, pigments and amino acids. Besides, structurants may also be present, besides nutrients, for example so as to improve the texture or the appearance of the feedstuff. Furthermore, it is also possible to employ, for example, binders so as to influence the consistency of the feedstuff. A component which is preferably employed and which constitutes both a nutrient and a structurant is starch.

According to the invention, a feedstuff according to the invention or a composition used to produce a feedstuff according to the invention is preferably distinguished by the fact that it contains a biomass according to the invention in an amount of 2 to 24% by weight, preferably 4 to 22% by weight, in particular 9 to 20% by weight, above all 11 to 18% by weight.

Said feedstuff or the composition used to produce the feedstuff preferably additionally has at least one, preferably all, of the following properties:
a) a total protein content of 33 to 67% by weight, preferably 39 to 61% by weight, in particular 44 to 55% by weight;
b) a total fat content of 5 to 25% by weight, preferably 8 to 22% by weight, in particular 10 to 20% by weight, above all 12 to 18% by weight;
c) a total starch content of at most 25% by weight, in particular at most 20% by weight, preferably 6 to 17% by weight, especially preferably 8 to 14% by weight;
d) a polyunsaturated fatty acid (PUFA) content of 2 to 13% by weight, preferably 3 to 11% by weight, in particular 4 to 10% by weight, above all 5.5 to 9% by weight;
e) an omega-3 fatty acid content of 1 to 7% by weight, preferably 1.5 to 5.5% by weight, in particular 2 to 5% by weight, above all 2.5 to 4.5% by weight;
f) a DHA content of 0.5 to 3% by weight, preferably 0.8 to 2.8% by weight, in particular 1 to 2.8% by weight, above all 1.3 to 2.4% by weight, in particular 1.3 to 2.2% by weight.

The invention therefore preferably also provides a feedstuff or a composition suitable for producing the feedstuff having at least one, preferably all, of the following properties:
a) a total protein content of 33 to 67% by weight, preferably 39 to 61% by weight, in particular 44 to 55% by weight;
b) a total fat content of 5 to 25% by weight, preferably 8 to 22% by weight, in particular 10 to 20% by weight, above all 12 to 18% by weight;
c) a total starch content of at most 25% by weight, in particular at most 20% by weight, preferably 6 to 17% by weight, especially preferably 8 to 14% by weight;
d) a polyunsaturated fatty acid (PUFA) content of 2 to 13% by weight, preferably 3 to 11% by weight, in particular 4 to 10% by weight, above all 5.5 to 9% by weight;
e) an omega-3 fatty acid content of 1 to 7% by weight, preferably 1.5 to 5.5% by weight, in particular 2 to 5% by weight, above all 2.5 to 4.5% by weight;
f) a DHA content of 0.5 to 3% by weight, preferably 0.8 to 2.8% by weight, in particular 1 to 2.8% by weight, above all 1.3 to 2.4% by weight, in particular 1.3 to 2.2% by weight.

The invention therefore preferably also provides a feedstuff or a composition suitable for producing the feedstuff having at least one, preferably all, of the following properties:
a) a total protein content of 33 to 67% by weight, preferably 39 to 61% by weight, in particular 44 to 55% by weight;
b) a total fat content of 5 to 25% by weight, preferably 8 to 22% by weight, in particular 10 to 20% by weight, above all 12 to 18% by weight;
c) a total starch content of at most 25% by weight, in particular at most 20% by weight, preferably 6 to 17% by weight, especially preferably 8 to 14% by weight;
d) a content of biomass according to the invention, in particular a Labyrinthulea biomass according to the invention, preferably a Thraustochytriaceae biomass according to the invention, of 2 to 24% by weight, preferably 4 to 22% by weight, in particular 9 to 20% by weight, above all 11 to 18% by weight;
e) a polyunsaturated fatty acid (PUFA) content of 2 to 13% by weight, preferably 3 to 11% by weight, in particular 4 to 10% by weight, above all 5.5 to 9% by weight;
f) an omega-3 fatty acid content of 1 to 7% by weight, preferably 1.5 to 5.5% by weight, in particular 2 to 5% by weight, above all 2.5 to 4.5% by weight;
g) a DHA content of 0.5 to 3% by weight, preferably 0.8 to 2.8% by weight, in particular 1 to 2.8% by weight, above all 1.3 to 2.4% by weight, in particular 1.3 to 2.2% by weight.

The invention therefore preferably also provides a feedstuff or a composition suitable for producing the feedstuff having at least one, preferably all, of the following properties:
a) a total protein content of 33 to 67% by weight, preferably 39 to 61% by weight, in particular 40 to 50% by weight;
b) a total fat content of 5 to 25% by weight, preferably 8 to 22% by weight, in particular 10 to 20% by weight, above all 12 to 18% by weight;
c) a total starch content of at most 25% by weight, in particular at most 20% by weight, preferably 6 to 17% by weight, especially preferably 8 to 14% by weight;

d) a content of an *Aurantiochytrium* biomass according to the invention, preferably an *Aurantiochytrium limacinum* biomass according to the invention, above all an *Aurantiochytrium limacinum* SR21 biomass according to the invention, of 2 to 24% by weight, preferably 4 to 22% by weight, in particular 9 to 20% by weight, above all 11 to 18% by weight;
e) a polyunsaturated fatty acid (PUFA) content of 2 to 13% by weight, preferably 3 to 11% by weight, in particular 4 to 10% by weight, above all 5.5 to 9% by weight;
f) an omega-3 fatty acid content of 1 to 7% by weight, preferably 1.5 to 5.5% by weight, in particular 2 to 5% by weight, above all 2.5 to 4.5% by weight;
g) a DHA content of 0.5 to 3% by weight, preferably 0.8 to 2.8% by weight, in particular 1 to 2.8% by weight, above all 1.3 to 2.4% by weight, in particular 1.3 to 2.2% by weight.

By extrusion of the above-mentioned compositions, it is possible to obtain an extrudate having an abrasion resistance of at least 91%, in particular at least 92, 93 or 94%. The present invention preferably provides said extrudates.

According to the invention, abrasion resistance was determined as follows: The dried extrudate (having a diameter of 4 mm and a length of 4 mm) was exposed to a mechanical load using the Holmen pellet tester NHP100 (Borregaard Lignotech, Hull, UK). Before carrying out the test, the samples were screened in order to remove any adherent fine particles. The processed samples (100 g) were subsequently introduced into the pellet tester using a 2.5 mm filter screen. The pellets were subsequently conveyed through a pipe having right-angled pipe bends at high air velocity (about 70 mbar) for 30 seconds. The experimental parameters are predetermined by the equipment. Subsequently, abrasion was determined by weighing. Abrasion resistance was specified as PDI (Pellet Durability Index), defined as the amount in percent of sample remaining in the filter screen after the test has been carried out. The test was carried out with three samples and then the mean was determined.

It proved to be especially advantageous according to the invention when the extrusion is done at an energy input of 12-28 Wh/kg, in particular 14-26 Wh/kg, especially preferably 16-24 Wh/kg, above all 18-22 Wh/kg.

In this connection, a screw or twin-screw extruder is preferably employed in the extrusion process. The extrusion process is preferably carried out at a temperature of 80-220° C., in particular 80-130° C., above all 95-110° C., a pressure of 10-40 bar, and a shaft rotational speed of 100-1000 rpm, in particular 300-700 rpm. The residence time of the mixture introduced is preferably 5-30 seconds, in particular 10-20 seconds.

The extrusion process may optionally comprise a compacting step and/or a compression step.

It is preferred to intimately mix the components with each other before carrying out the extrusion process. This is preferably carried out in a drum equipped with vanes. In a preferred embodiment, this mixing step includes an injection of steam, in particular so as to bring about swelling of the starch which is preferably present. In this case, the injection of steam is carried out preferably at a pressure of 1 to 5 bar, especially preferably at a pressure of 2 to 4 bar.

Before being mixed with the algae biomass, the further foodstuff or feedstuff ingredients are preferably comminuted—if required—so as to ensure that a homogeneous mixture is obtained in the mixing step. The comminuting of the further foodstuff or feedstuff ingredients may be carried out, for example, using a hammer mill.

The extrudate created preferably has a diameter of 1 to 14 mm, preferably 2 to 12 mm, in particular 2 to 6 mm, and preferably also has a length of 1 to 14 mm, preferably 2 to 12 mm, in particular 2 to 6 mm. The length of the extrudate is set during extrusion by using a cutting tool. The length of the extrudate is preferably selected such that it approximately corresponds to the diameter of the extrudate. The diameter of the extrudate is defined by selecting the screen diameter.

In one embodiment preferred according to the invention, the extrusion process is followed by the extrudate obtained being loaded with oil. To this end, the extrudate is preferably initially dried to a moisture content of at most 5% by weight. According to the invention, the extrusion product may be loaded with oil by, for example, placing the extrudate in oil or spraying the extrudate with oil; however, according to the invention, preference is given to vacuum coating.

In this way, feedstuffs are obtained which contain biomasses according to the invention preferably in an amount of 2 to 22% by weight, in particular 4 to 20% by weight, especially preferably 8 to 18% by weight, above all 10 to 16% by weight.

Accordingly, said feedstuffs preferably additionally have at least one, preferably all, of the following properties:
a) a total protein content of 30 to 60% by weight, preferably 35 to 55% by weight, in particular 40 to 50% by weight;
b) a total fat content of 15 to 35% by weight, preferably 18 to 32% by weight, in particular 20 to 30% by weight, above all 22 to 28% by weight;
c) a total starch content of at most 25% by weight, in particular at most 20% by weight, preferably 5 to 15% by weight, especially preferably 7 to 13% by weight;
d) a polyunsaturated fatty acid (PUFA) content of 2 to 12% by weight, preferably 3 to 10% by weight, in particular 4 to 9% by weight, above all 5 to 8% by weight;
e) an omega-3 fatty acid content of 1 to 6% by weight, preferably 1.5 to 5% by weight, in particular 2 to 4.5% by weight, above all 2.5 to 4% by weight;
f) a DHA content of 0.5 to 3% by weight, preferably 0.8 to 2.5% by weight, in particular 1 to 2.5% by weight, above all 1.2 to 2.2% by weight, in particular 1.2 to 2.0% by weight.

The invention therefore preferably also provides a feedstuff, in particular an extrudate, having at least one, preferably all, of the following properties:
a) a total protein content of 30 to 60% by weight, preferably 35 to 55% by weight, in particular 40 to 50% by weight;
b) a total fat content of 15 to 35% by weight, preferably 18 to 32% by weight, in particular 20 to 30% by weight, above all 22 to 28% by weight;
c) a total starch content of at most 25% by weight, in particular at most 20% by weight, preferably 5 to 15% by weight, especially preferably 7 to 13% by weight;
d) a polyunsaturated fatty acid (PUFA) content of 2 to 12% by weight, preferably 3 to 10% by weight, in particular 4 to 9% by weight, above all 5 to 8% by weight;
e) an omega-3 fatty acid content of 1 to 6% by weight, preferably 1.5 to 5% by weight, in particular 2 to 4.5% by weight, above all 2.5 to 4% by weight;
f) a DHA content of 0.5 to 3% by weight, preferably 0.8 to 2.5% by weight, in particular 1 to 2.5% by weight, above all 1.2 to 2.2% by weight, in particular 1.2 to 2.0% by weight.

The invention therefore preferably also provides a feedstuff, in particular an extrudate, having at least one, preferably all, of the following properties:
a) a total protein content of 30 to 60% by weight, preferably 35 to 55% by weight, in particular 40 to 50% by weight;
b) a total fat content of 15 to 35% by weight, preferably 18 to 32% by weight, in particular 20 to 30% by weight, above all 22 to 28% by weight;
c) a total starch content of at most 25% by weight, in particular at most 20% by weight, preferably 5 to 15% by weight, especially preferably 7 to 13% by weight;
d) a content of a biomass according to the invention, in particular a Labyrinthulea biomass according to the invention, preferably a Thraustochytriaceae biomass according to the invention, of 2 to 22% by weight, preferably 4 to 20% by weight, in particular 8 to 18% by weight, above all 10 to 16% by weight;
e) a polyunsaturated fatty acid (PUFA) content of 2 to 12% by weight, preferably 3 to 10% by weight, in particular 4 to 9% by weight, above all 5 to 8% by weight;
f) an omega-3 fatty acid content of 1 to 6% by weight, preferably 1.5 to 5% by weight, in particular 2 to 4.5% by weight, above all 2.5 to 4% by weight;
g) a DHA content of 0.5 to 3% by weight, preferably 0.8 to 2.5% by weight, in particular 1 to 2.5% by weight, above all 1.2 to 2.2% by weight, in particular 1.2 to 2.0% by weight.

The invention therefore preferably also provides a feedstuff, in particular an extrudate, having at least one, preferably all, of the following properties:
a) a total protein content of 30 to 60% by weight, preferably 35 to 55% by weight, in particular 40 to 50% by weight;
b) a total fat content of 15 to 35% by weight, preferably 18 to 32% by weight, in particular 20 to 30% by weight, above all 22 to 28% by weight;
c) a total starch content of at most 25% by weight, in particular at most 20% by weight, preferably 5 to 15% by weight, especially preferably 7 to 13% by weight;
h) a content of an *Aurantiochytrium* biomass according to the invention, preferably an *Aurantiochytrium limacinum* biomass according to the invention, above all an *Aurantiochytrium limacinum* SR21 biomass according to the invention, of 2 to 22% by weight, preferably 4 to 20% by weight, in particular 8 to 18% by weight, above all 10 to 16% by weight;
d) a polyunsaturated fatty acid (PUFA) content of 2 to 12% by weight, preferably 3 to 10% by weight, in particular 4 to 9% by weight, above all 5 to 8% by weight;
e) an omega-3 fatty acid content of 1 to 6% by weight, preferably 1.5 to 5% by weight, in particular 2 to 4.5% by weight, above all 2.5 to 4% by weight;
f) a DHA content of 0.5 to 3% by weight, preferably 0.8 to 2.5% by weight, in particular 1 to 2.5% by weight, above all 1.2 to 2.2% by weight, in particular 1.2 to 2.0% by weight.

The present invention preferably further provides the above-mentioned extrudates obtainable by oil coating and having preferably a water stability of at least 96%, in particular at least 97 or 98%.

Water stability was essentially determined as described by Baeverfjord et al. (2006; Aquaculture 261, 1335-1345), with slight modifications. 10 g samples of the extrudate (having a length and a diameter of 4 mm in each case) were introduced into metallic infusion baskets (Inox, Germany) having a diameter of 6.5 mm and a mesh size of 0.3 mm. The infusion baskets were subsequently introduced into a plastic trough containing water, and so the samples were completely covered with water. The trough was subsequently exposed for 30 minutes to a shake-agitation of 30 shake units per minute using the Multiorbital shaker PSU-201 (Biosan, Latvia). Thereafter, the samples were carefully dried with blotting paper and then weighed before and after they had been subjected to oven-drying at a temperature of 105° C. for 24 hours. Water stability was calculated as the difference in the dry weight of the sample before and after the incubation in water and specified in percent of the dry weight of the sample used before the incubation with water.

According to the invention, the fat-containing component used may be, besides the biomass to be used according to the invention, fats, in particular oils, of both animal and plant origin. According to the invention, suitable fat-containing components are in particular vegetable oils, for example soya bean oil, rapeseed oil, sunflower seed oil, flaxseed oil or palm oil and mixtures thereof. In addition, fish oil may also optionally be used as fat-containing component in low amounts.

Preferably, a feedstuff according to the invention having an abrasion resistance of at least 96, 97 or 98% contains vegetable oils in an amount of 3 to 18% by weight, in particular 5 to 15% by weight, above all 7 to 13% by weight. As described above, the vegetable oil is in this connection preferably applied to the extrudate in a subsequent manner, in particular by vacuum coating.

According to the invention, the protein-containing component used may be, for example, soya protein, pea protein, wheat gluten or corn gluten and mixtures thereof.

The following examples may be employed as a protein-containing component which additionally contains fats: fish meal, krill meal, bivalve meal, squid meal or shrimp shells. These are hereinafter subsumed under the term "marine meal". In a preferred embodiment, a feedstuff according to the invention comprises marine meal, preferably fish meal, in an amount of 3 to 18% by weight, in particular 5 to 15% by weight, above all 7 to 13% by weight.

The carbohydrate-containing component used may be, for example, wheat meal, sunflower meal or soya meal and mixtures thereof.

When using feedstuffs according to the invention, in particular an oil-coated extrudate according to the invention, in animal farming, it became apparent that this especially promoted the growth of the animals and improved the stress level of the animals.

The present invention also further provides a method for farming animals, characterized in that they are administered with a feedstuff according to the invention.

In this connection, the present invention provides in particular a method for increasing the growth of animals, characterized in that they are administered with a feedstuff according to the invention.

The present invention further provides in particular similarly a method for increasing the fraction of omega-3 fatty acids, in particular DHA, in the muscle tissue of animals, characterized in that they are administered with a feedstuff according to the invention.

Preferably, in the process according to the invention, the feedstuff is administered at least every two days, preferably at least once daily.

The present invention further provides similarly the use of a feedstuff according to the invention for increasing growth in animals.

The present invention further provides likewise the use of a feedstuff according to the invention for increasing the fraction of omega-3 fatty acids in muscle tissue in animals.

The present invention further provides likewise the use of a feedstuff according to the invention for improving the physical condition of animals, in particular for improving the stress level of animals.

The present invention further provides likewise the use of a feedstuff according to the invention for allowing a stress-reduced farming of the animals.

The farmed animals fed with a feedstuff according to the invention are preferably poultry, pigs or cattle.

However, the farmed animals are especially preferably marine animals, especially preferably finfish or crustaceans. These include, in particular, carp, tilapia, catfish, tuna, salmon, trout, barramundi, bream, perch, cod, shrimps, lobster, crabs, prawns and crayfish. The farmed animals are especially preferably salmon. Preferred types of salmon in this context are the Atlantic salmon, red salmon, masu salmon, king salmon, keta salmon, coho salmon, Danube salmon, Pacific salmon and pink salmon.

The farmed animals may in particular also be fish which are subsequently processed into fish meal or fish oil. In this connection, the fish are preferably herring, pollack, menhaden, anchovies, capelin or cod. The fish meal or fish oil thus obtained, in turn, can be used in aquaculture for farming edible fish or crustaceans.

However, the farmed animals may also be small organisms which are used as feedstuff in aquaculture. These small organisms may take the form of, for example, nematodes, crustaceans or rotifers.

The farming of marine animals may take place in ponds, tanks, basins or else in segregated areas in the sea or in lakes, in particular in this case in cages or net pens. Farming may be used for farming the finished edible fish, but also may be used for farming fry which are subsequently released so as to restock the wild fish stocks.

In salmon farming, the fish are preferably first grown into smolts in freshwater tanks or artificial watercourses and then grown on in cages or net pens which float in the sea and which are preferably anchored in bays or fjords.

Accordingly, the feedstuff according to the invention is preferably a feedstuff for use in the farming of the above-mentioned animals.

WORKING EXAMPLES

Example 1

Producing Biomass by Fermentation of *Aurantiochytrium limacinum* SR21 in Media of Differing Sodium Sulphate Content The cells were cultured for about 75 h in a feed process using a steel fermenter having a fermenter volume of 2 litres with a total starting mass of 712 g and an attained total final mass of 1.3-1.5 kg. During the process, a glucose solution (570 g/kg glucose) was metered in (fed-batch process)

The composition of the starting media was as follows:

Medium 1: 20 g/kg glucose; 4 g/kg yeast extract; 2 g/kg ammonium sulphate; 2.46 g/kg magnesium sulphate (heptahydrate); 0.45 g/kg potassium chloride; 4.5 g/kg potassium dihydrogen phosphate; 0.1 g/kg thiamine (HCl); 5 g/kg trace element solution.

Medium 2: As per medium 1 plus 8 g/kg sodium sulphate
Medium 3: As per medium 1 plus 12 g/kg sodium sulphate
Medium 4: As per medium 1 plus 16 g/kg sodium sulphate The composition of the trace element solution was as follows: 35 g/kg hydrochloric acid (37%); 1.86 g/kg manganese chloride (tetrahydrate); 1.82 g/kg zinc sulphate (heptahydrate); 0.818 g/kg sodium EDTA; 0.29 g/kg boric acid; 0.24 g/kg sodium molybdate (dihydrate); 4.58 g/kg calcium chloride (dihydrate); 17.33 g/kg iron sulphate (heptahydrate); 0.15 g/kg copper chloride (dihydrate).

Culturing was carried out under the following conditions: Culture temperature 28° C.; aeration rate 0.5 vvm, stirrer speed 600-1950 rpm, control of pH in the growth phase at 4.5 using ammonia water (25% v/v). The following biomass densities were achieved: 100 g/l (medium 1), 111 g/l (medium 2), 114 g/l (medium 3), 116 g/l (medium 4). The viscosity of the resulting fermentation broth distinctly increased with increasing sulphate content, and this is evidence of the increase in the EPS content in the particular resulting fermentation broth.

After the culturing process, the fermentation broths were heated to 60° C. for 20 minutes in order to prevent further cellular activity.

Example 2

Determining the DHA Content of the Biomasses

After inactivation, the biomasses obtained were subjected to a fatty acid analysis. To this end, 0.2-0.5 ml of each fermentation broth was admixed with 1 ml of internal standard and topped up with 9 ml of a methanol/chloroform solution (1:2; v/v). The samples were treated for 10 min in an ultrasonic bath. Subsequently, the samples were concentrated to dryness under a nitrogen blanket at 50° C. in a thermal block. 2 ml of 0.5 N KOH were added to each of the residues of drying and incubated at 100° C. for 15 min. Subsequently, the samples were cooled down to room temperature, admixed with, in each case, 2 ml of 0.7 N HCl and 1 ml of boron trifluoride solution (14% BF3 in methanol) and incubated at 100° C. for a further 15 min. After cooling down to room temperature, the samples were each extracted with a mixture composed of 3 ml of water and 2 ml of heptane. After centrifugation for 1 min at 2000 rpm, 1 ml from each upper phase was transferred to a GC vial and analysed by gas chromatography.

The analysis revealed that all four biomasses contained a DHA fraction of more than 32% by weight with regard to the total amount of fatty acids present.

Example 3

Drying the Biomasses Obtained

The cooled-down biomass-containing fermentation broths having different contents of $Na_2SO_4$ according to Example 1 were each separately subjected to spray drying.

Spray drying was carried out in each case using a Büchi mini spray dryer B-290 (diameter of nozzle tip: 0.7 mm; flow rate of spray air: 742 L/h; flow rate of aspirator: 35 m³/h; temperature of inlet air: 220° C.; temperature of outlet air: 80° C.).

Example 4

Determining the Sulphate and DHA Contents of the Spray-Dried Samples

The samples obtained by spray drying the fermentation broths having different contents of Na2SO4 were subjected to a sulphate or sulphur determination and a DHA concentration determination. DHA determination was carried out as described under Example 2. Sulphur content was determined in accordance with DIN EN ISO 11885.

TABLE 1

Analysis of spray-dried samples

| Property | Starting medium of the fermentation broth used for spray drying | | | |
|---|---|---|---|---|
| | Medium 1 | Medium 2 | Medium 3 | Medium 4 |
| Sulphur in accordance with DIN EN ISO 11885 | 3.60 g/kg | 7.72 g/kg | 10.0 g/kg | 11.0 g/kg |
| DHA content | 16.6% | 15.6% | 16.0% | 16.0% |

The determination of the sulphur content confirms that, with increasing sulphate content in the fermentation medium, more and more sulphate was also incorporated into the obtainable biomass, and this is further evidence of the greatly increased formation of EPS.

Example 4

Determining the Caking Tendency

The fermentation broths obtained after fermentation in media having different contents of sodium sulphate exhibited distinct differences in the spray drying process and the spray-dried material obtained exhibited varying caking tendency, the basis of this being released oil. The biomasses obtained by fermentation in media 3 and 4 showed a distinctly lower caking tendency than the biomasses obtained by fermentation in media 1 and 2. This is evidence of the cell stability of the cells in the biomasses concerned that is increased as a result of increased EPS formation.

Example 5

Drying the Sulphate-Rich Biomass from Example 1 for the Purpose of Feedstuff Production The biomass from Example 1 obtained in the sulphate-rich medium 4 was subjected to a two-stage drying process for the purpose of producing feedstuffs: Firstly, the fermentation broth was concentrated by evaporation to a dry mass of about 20% by weight. This was followed by spray drying of the concentrated fermentation broth using a Production Minor™ spray dryer (GEA NIRO) at a drying air inlet temperature of 340° C. By means of spray drying, a powder having a dry mass of more than 95% by weight was thus obtained.

Example 6

Producing a Feedstuff by Extrusion

The feedstuff mixtures shown in Table 3 were produced. Besides the biomass to be used according to the invention as per Example 5, two further commercially available Labyrinthulea biomasses and also fish oil as a currently still customary source of omega-3 fatty acids were tested for comparison.

The feedstuff mixtures were each produced by mixing of the components—with the exception of the oils—using a double-helix mixer (model 500L, TGC Extrusion, France). The mixtures thus obtained were then comminuted to particle sizes below 250 μm using a hammer mill (model SH1, Hosokawa-Alpine, Germany).

TABLE 2

Feedstuff compositions used in the extrusion process (data in % by weight)

| Ingredient | M1 | M2 | M3 | M4 |
|---|---|---|---|---|
| Fish meal | 10.00 | 10.00 | 10.00 | 10.00 |
| Soya protein concentrate | 23.10 | 23.20 | 23.10 | 20.27 |
| Pea protein concentrate | 15.00 | 15.00 | 15.00 | 15.00 |
| Wheat gluten | 9.90 | 9.90 | 9.90 | 9.90 |
| Wheat meal | 18.12 | 10.82 | 10.55 | 16.46 |
| Fish oil | 10.00 | — | — | — |
| Biomass from Example 1 | — | 16.00 | — | — |
| Commercially available biomass 1 | — | — | 16.74 | — |
| Commercially available biomass 2 | — | — | — | 13.52 |
| Rape oil | 10.00 | 11.00 | 11.00 | 11.00 |
| Vitamin/mineral premix | 1.00 | 1.00 | 1.00 | 1.00 |
| DCP | 2.00 | 2.00 | 2.00 | 2.00 |
| Yttrium oxide | 0.03 | 0.03 | 0.03 | 0.03 |
| DL-Methionine | 0.35 | 0.36 | 0.33 | 0.33 |
| Aquavi Lys | 0.17 | 0.35 | 0.08 | 0.19 |
| TrypAmino | 0.09 | 0.09 | 0.08 | 0.09 |
| L-Histidine | 0.24 | 0.25 | 0.19 | 0.21 |

For the extrusion process, use was made in each case of 140 kg per feedstuff. The extrusion process was carried out using a twin-screw extruder (CLEXTRAL BC45) having a screw diameter of 55.5 mm and a maximum flow rate of 90-100 kg/h. Pellets of 4.0 mm in size (diameter and length) were extruded. To this end, the extruder was equipped with a high-speed cutter in order to convert the product to the intended pellet size.

Various extrusion parameters were then tested in order to find out under what extrusion conditions it is possible to obtain an optimal oil load capacity of the extrudate obtained. In this connection, it became apparent that, surprisingly, an optimal oil load capacity can be achieved with a very low energy input. In this connection, the energy input was distinctly lower than when using fish oil. Furthermore, the optimal energy input in the case of an algae biomass to be preferably used according to the invention was again distinctly lower than in the case of commercially available algae biomasses. The results are shown in Table 3.

TABLE 3

Energy inputs relating to producing pellets having the desired oil load capacity

| Diet | Barrel 1 Temp (° C.) | Barrel 2 Temp (° C.) | Feeder rate (kg/h) | Rotational speed (rpm) | Amount of water (0-10) | Current (A) | SME (Wh/kg) |
|---|---|---|---|---|---|---|---|
| M1 | 31 | 116-118 | 112 | 215 | 9 | 11 | 34.6 |
| M2 | 32 | 98-104 | 141 | 253 | 5 | 7 | 20.6 |
| M3 | 32 | 97-102 | 136 | 255 | 5 | 8 | 24.6 |
| M4 | 31 | 99-107 | 133 | 253 | 5 | 8 | 24.9 |

In this connection, the variable "SME" is the specific mechanical energy. This is calculated as follows:

$$SME \text{ (Wh/kg)} = \frac{U \times I \times \cos \Phi \frac{\text{Test } SS}{\text{Max } SS}}{Qs}$$

where
U: operating voltage of the motor (here 460 V)
I: current of the motor (A)
cos φ: theoretical performance of the extruder motor (here 0.95)
Test SS: test speed (rpm) of the rotating screws
Max SS: maximum speed (267 rpm) of the rotating screws
$Q_s$: inlet flow rate of the mash (kg/h)

After extrusion, the extrudate was dried in a vibrating fluidized bed dryer (model DR100, TGC Extrusion, France).

This was followed, after the extrudate had cooled down, by an oil coating process by means of vacuum coating (vacuum coater PG-10VCLAB, Dinnisen, the Netherlands).

Example 7

Ascertaining the Abrasion Resistance and Water Stability of the Feedstuffs from Example 6

Abrasion resistance was ascertained as follows: Before being loaded with oil, the dried extrusion product was exposed to a mechanical load using the Holmen pellet tester (Borregaard Lignotech, Hull, UK). Before carrying out the test, the samples were screened in order to remove any adherent fine particles. The processed samples (100 g) were subsequently introduced into the pellet tester using a 2.5 mm filter screen. The pellets were subsequently conveyed through a pipe having right-angled pipe bends at high air velocity for 30 seconds. Subsequently, abrasion was determined by weighing. Abrasion resistance was specified as PDI (Pellet Durability Index), defined as the amount in percent of sample remaining in the filter screen. The test was carried out with three samples and then the mean was determined.

Water stability was carried out using the oil-loaded samples. The method was essentially carried out as described by Baeverfjord et al. (2006; Aquaculture 261, 1335-1345), with slight modifications. 10 g samples were introduced into metallic infusion baskets having a mesh size of 0.3 mm. The infusion baskets were subsequently introduced into a plastic trough containing water, and so the samples were completely covered with water. The trough was subsequently exposed for 30 minutes to a shake-agitation of 30 shake units per minute. Thereafter, the samples were carefully dried with blotting paper and then weighed before and after they had been subjected to oven-drying at a temperature of 105° C. for 24 hours. Water stability was calculated as the difference in the dry weight of the sample before and after the incubation in water and specified in percent of the dry weight of the sample used before the incubation with water.

The results are shown in Table 4 below.

| Sample | M1 | M2 | M3 | M4 |
| --- | --- | --- | --- | --- |
| Abrasion resistance [%] | 90.0 | 93.3 | 88.3 | 85.2 |
| Water stability [%] | 95.7 | 98.5 | 93.8 | 90.2 |

It can be seen that a feedstuff according to the invention which contains a biomass according to the invention having a high EPS content has a distinctly higher abrasion resistance and water stability than feedstuffs which contain a commercially available Labyrinthulea biomass or fish oil as a source of omega-3 fatty acids.

The invention claimed is:

1. A biomass dried comprising: exopolysaccharides (EPSs) of microorganisms of the taxon Labyrinthulomycetes, wherein the biomass has and a sulphate content, based on the dry mass, of 25 to 60 g/kg.

2. The biomass of claim 1, wherein said biomass has a sulphate content, based on the dry mass, of 25 to 40 g/kg.

3. The biomass of claim 1, wherein the microorganisms of the taxon Labyrinthulomycetes are of the family Thraustochytriaceae.

4. The biomass of claim 3, wherein the microorganisms of the taxon Labyrinthulomycetes are of the genus *Althomia, Aplanochytrium, Elnia, Japonochytrium, Schizochytrium, Thraustochytrium, Aurantiochytrium, Oblongichytrium* or *Ulkenia*.

5. The biomass of claim 4, wherein the microorganisms are of the genus *Aurantiochytrium*.

6. The biomass of claim 5, wherein the microorganisms are of species *Aurantiochytrium limacinum*.

7. A feedstuff, comprising the biomass of claim 1.

8. The feedstuff of claim 7, wherein said feedstuff comprises:
a) a total protein content of 30 to 60% by weight;
b) a total fat content of 15 to 35% by weight;
c) a total starch content of at most 25% by weight; and
d) a biomass content of 2 to 22% by weight.

9. The feedstuff of claim 8, wherein said feedstuff comprises:
e) a polyunsaturated fatty acid (PUFA) content of 2 to 12% by weight.

10. The feedstuff of claim 8, wherein said feedstuff comprises:
f) an omega-3 fatty acid content of 1 to 6% by weight.

11. The feedstuff of claim 8, wherein said feedstuff comprises:
g) a DHA content of 0.5 to 3% by weight.

12. The feedstuff of claim 9, wherein said feedstuff comprises:
f) an omega-3 fatty acid content of 1 to 6% by weight; and
g) a DHA content of 0.5 to 3% by weight.

13. The feedstuff of claim 7, wherein said feedstuff comprises:
a) a total protein content of 40 to 50% by weight;
b) a total fat content of 20 to 30% by weight;
c) a total starch content of 5 to 15% by weight;
d) a biomass content of 8 to 18% by weight.

14. The feedstuff of claim 13, further comprising one or more of the following:
e) a polyunsaturated fatty acid (PUFA) content of 5 to 8% by weight;
f) an omega-3 fatty acid content of 2.5 to 4% by weight;
g) a DHA content of 1.2 to 2.0% by weight.

15. The biomass of claim 1, comprising a sulphate content, based on the dry mass, of 25 to 30 g/kg.

16. The biomass of claim 15, wherein the microorganisms of the taxon Labyrinthulomycetes are of the family Thraustochytriaceae.

17. The biomass of claim 15, wherein the microorganisms are cells of the species *Aurantiochytrium limacinum*.

18. The feedstuff of claim 8, wherein said biomass comprises a sulphate content, based on the dry mass, of 25 to 30 g/kg.

19. The feedstuff of claim 18, wherein said feedstuff comprises: a polyunsaturated fatty acid (PUFA) content of 2 to 12% by weight.

20. The feedstuff of claim 19, wherein said feedstuff comprises an omega-3 fatty acid content of 1 to 6% by weight.

* * * * *

UNITED STATES PATENT AND TRADEMARK OFFICE
CERTIFICATE OF CORRECTION

PATENT NO. : 10,842,174 B2
APPLICATION NO. : 15/516058
DATED : November 24, 2020
INVENTOR(S) : Thomas Durhuus et al.

Page 1 of 1

It is certified that error appears in the above-identified patent and that said Letters Patent is hereby corrected as shown below:

In the Claims

Column 18, Lines 2-5, Claim 1, are corrected to read as follows:
--1. A dried biomass comprising: exopolysaccharides (EPSs) of microorganisms of the taxon Labyrinthulomycetes, wherein the biomass has a sulphate content, based on the dry mass, of 25 to 60 g/kg.--

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*